(12) United States Patent
Chen et al.

(10) Patent No.: US 11,737,702 B1
(45) Date of Patent: Aug. 29, 2023

(54) WEARABLE PASSIVE SWEAT DETECTION DEVICE

(71) Applicant: SOOCHOW UNIVERSITY, Suzhou (CN)

(72) Inventors: Liguo Chen, Suzhou (CN); Hao Shen, Suzhou (CN); He Wang, Yihuai (CN); Haibo Huang, Suzhou (CN); Yan Pang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 18/027,107

(22) PCT Filed: Oct. 24, 2022

(86) PCT No.: PCT/CN2022/126989
§ 371 (c)(1),
(2) Date: Mar. 19, 2023

(30) Foreign Application Priority Data

May 6, 2022 (CN) .......................... 202210488546.0

(51) Int. Cl.
*A61B 5/00* (2006.01)
*A61B 10/00* (2006.01)

(52) U.S. Cl.
CPC .......... *A61B 5/4266* (2013.01); *A61B 5/6802* (2013.01); *A61B 10/0064* (2013.01)

(58) Field of Classification Search
CPC . A61B 5/4266; A61B 5/6802; A61B 10/0064; A61B 5/14517; A61B 5/14546; A61B 2217/005; A61B 2560/0406; A61B 5/4875; A61B 5/0537; A61B 5/1477
See application file for complete search history.

(56) References Cited

U.S. PATENT DOCUMENTS

| | | | |
|---|---|---|---|
| 2020/0107758 | A1 | 4/2020 | Lenigk et al. |
| 2020/0405273 | A1 | 12/2020 | Seyama et al. |
| 2021/0267502 | A1 | 9/2021 | Gurski et al. |

FOREIGN PATENT DOCUMENTS

| | | |
|---|---|---|
| CN | 105510388 A | 4/2015 |
| CN | 106694065 A | 5/2017 |
| CN | 109646015 A | 4/2019 |
| CN | 111624248 A | 9/2020 |
| CN | 111671437 A | 9/2020 |
| CN | 112129349 A | 12/2020 |
| CN | 114740060 A | 7/2022 |
| EP | 3431004 A1 | 1/2019 |

*Primary Examiner* — Patrick Fernandes
(74) *Attorney, Agent, or Firm* — SZDC LAW P.C.

(57) ABSTRACT

A wearable passive sweat detection device includes at least one detection sensor that includes: a base plate; a sensing element provided on the base plate, the sensing element including a sweat collection portion and a sweat self-driven detection portion, the sweat collection portion being configured to collect sweat discharged by sweat glands of skin, the sweat self-driven detection portion including a guide portion of a semi-conical structure, a test electrode provided on an outer conical surface of the guide portion, and a back electrode, and a narrow end of the guide portion facing the sweat collection portion; and a test element connected with the test electrode and back electrode. The adoption of the conical structure achieves a liquid-solid friction effect to realize passive detection of sweat components; meanwhile, flexibility is realized to facilitate wearing; by using different ion selective films, different ion concentrations can be detected; detection precision is high.

10 Claims, 7 Drawing Sheets

WEARABLE PASSIVE SWEAT DETECTION DEVICE

This application is the National Stage Application of PCT/CN2022/126989, filed on Oct. 24, 2022, which claims priority to Chinese Patent Application No. 202210488546.0, filed on May 6, 2022, which is incorporated by reference for all purposes as if fully set forth herein.

FIELD OF THE DISCLOSURE

The present invention relates to the field of sweat detection technologies, and particularly to a wearable passive sweat detection device based on a liquid-solid friction effect.

BACKGROUND OF THE DISCLOSURE

An increasing pace of life and an increasing working stress in modern society lead to an incidence increased year by year and a younger trend of numerous chronic diseases. As an object easy to obtain and suitable for long-term monitoring, sweat becomes a new object reflecting human body indexes, and research on wearable sweat detection gradually becomes a hot spot of wearable medical apparatuses.

Currently, there mainly exist two types of common sweat detection methods: electrochemical methods and chemical colorimetry. The electrochemical methods include cyclic voltammetry, a potentiometric method, a field effect transistor and impedance titration. The chemical colorimetry includes fluorescence detection and color reaction detection. Power and a relatively complex circuit design are required in the electrochemical method, long-term stable power supply is required by a real-time monitoring apparatus, and if a battery has low endurance and is required to be charged frequently, a user is likely to feel uncomfortable, and the battery has potential safety hazards in some special environments. An additional optical analysis apparatus is required in the chemical colorimetry. These defects limit wearability of the traditional methods.

SUMMARY OF THE DISCLOSURE

In order to overcome defects in a prior art, an object of the present invention is to provide a wearable passive sweat detection device.

A wearable passive sweat detection device, comprising at least one detection sensor, wherein the detection sensor comprises:
 a base plate;
 a sensing element provided on the base plate, the sensing element comprising a sweat collection portion and a sweat self-driven detection portion, the sweat collection portion being configured to collect sweat discharged from sweat glands of skin, the sweat self-driven detection portion comprising a guide portion of a semi-conical structure, a test electrode provided on an outer conical surface of the guide portion and a back electrode, and a narrow end of the guide portion facing the sweat collection portion;
 a test element connected with the test electrode and the back electrode.

The present invention has the beneficial effects as follows.
(1) Passive detection of sweat components is realized with a liquid-solid friction effect.
(2) Utilization of a cactus-like conical structure realizes directional movement of liquid drops, thereby realizing liquid-solid friction.
(3) Utilization of the PDMS as a main material of the sensing element achieves the liquid-solid friction effect, and meanwhile realizes flexibility to facilitate wearing.
(4) By using different ion selective films, different ion concentrations can be detected.
(5) A single liquid drop can be analyzed using the device, and detection precision is high. Since the liquid drop is a closed reaction cavity and has an independent liquid environment, compared with a continuous flow control technology, the liquid drop has a higher specific surface area, a temperature difference between an interior and an exterior of the liquid drop is greater, a mass transfer efficiency is higher, and a diffusion distance is shorter; that is, a dispersion degree of molecules in liquid is smaller and a pollution degree is lower, thereby improving detection accuracy.

Figure 1:
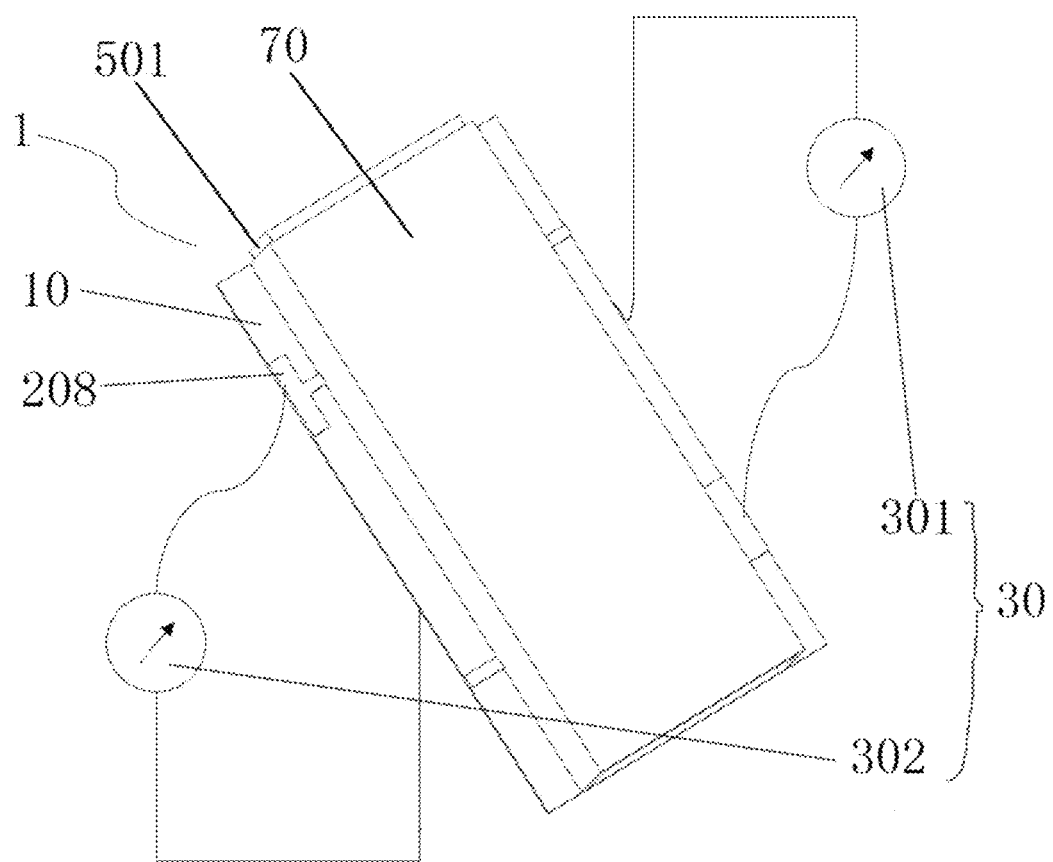
FIG. 1 is a schematic structural diagram of a preferred embodiment of the present invention.
Figure 2:
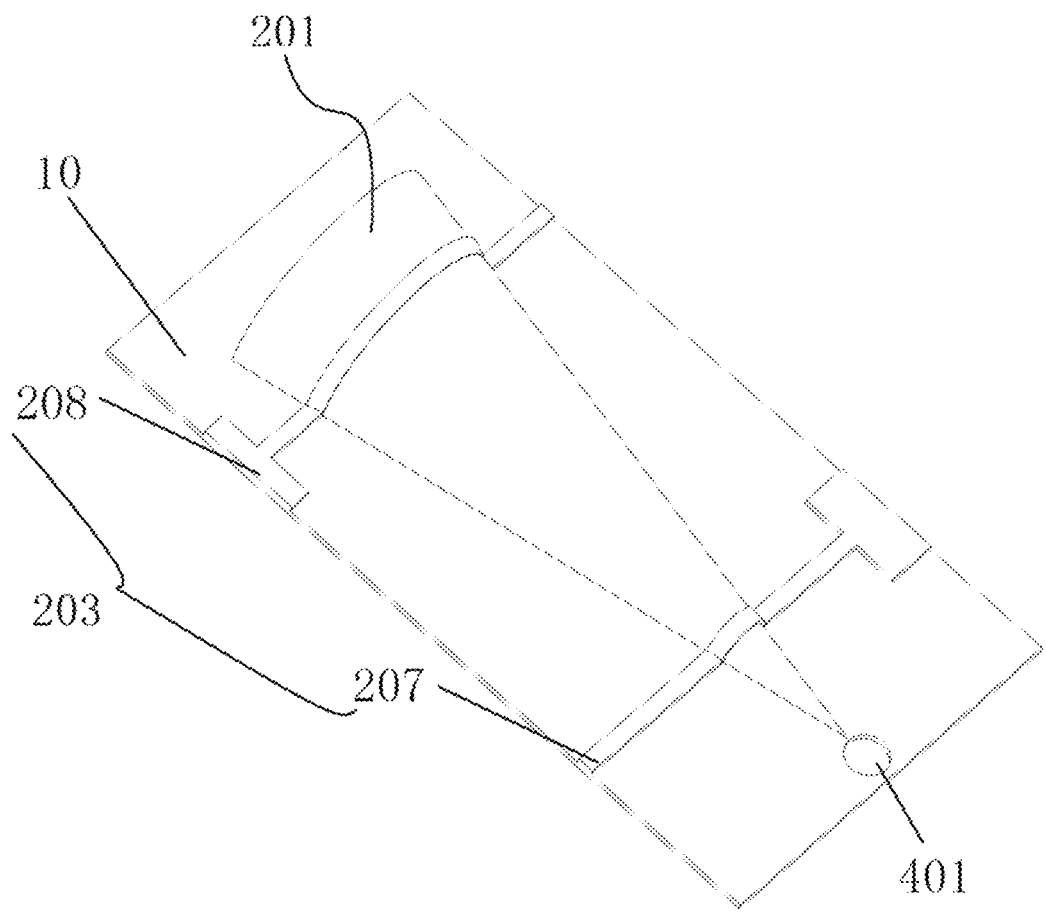
FIG. 2 is a schematic structural diagram of the preferred embodiment of the present invention without a protective shell.
Figure 3:
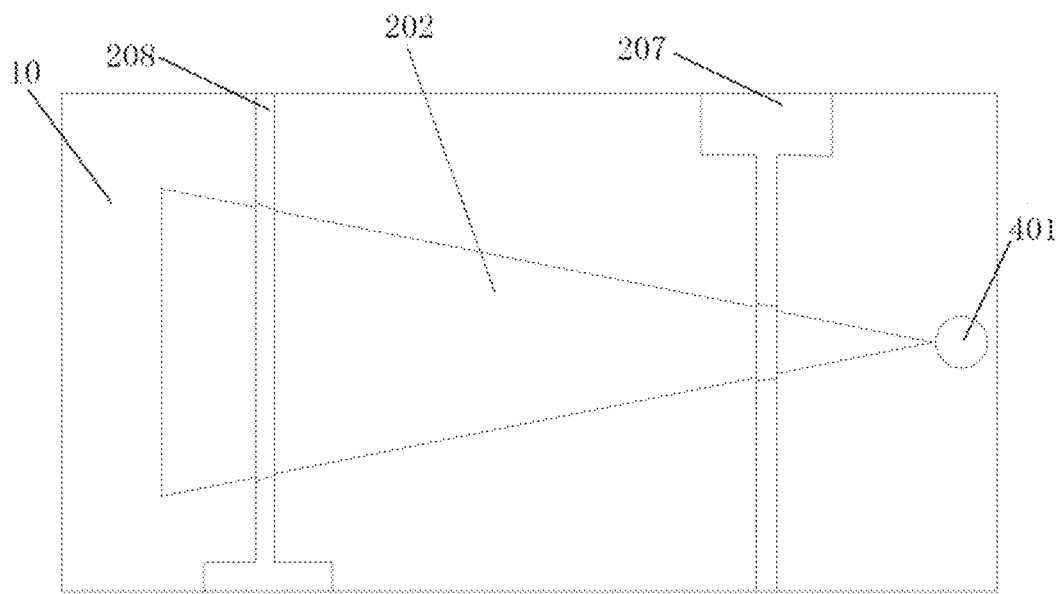
FIG. 3 is a top view of the preferred embodiment of the present invention without the protective shell.
Figure 4:
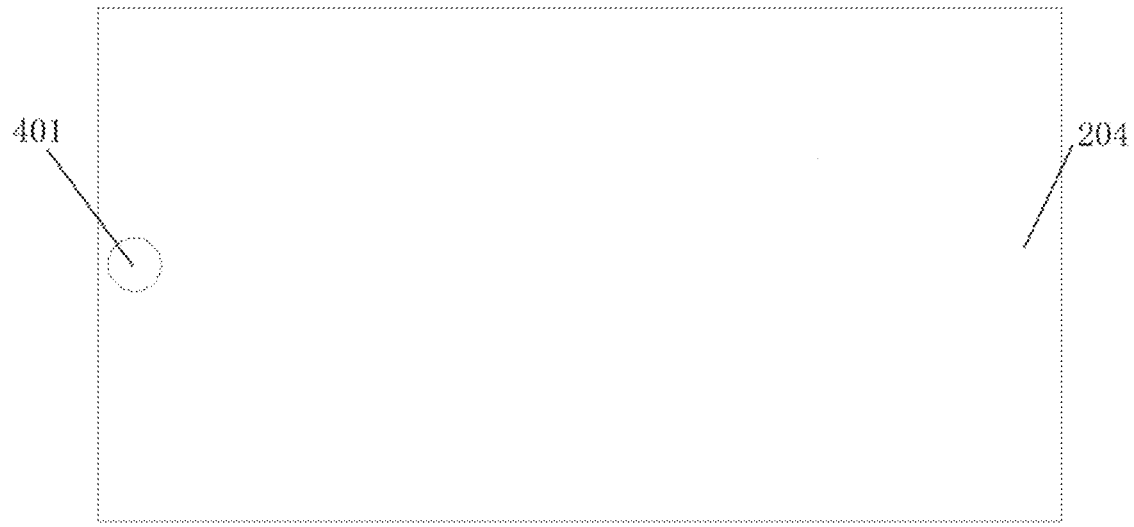
FIG. 4 is a bottom view of the preferred embodiment of the present invention.
Figure 5:
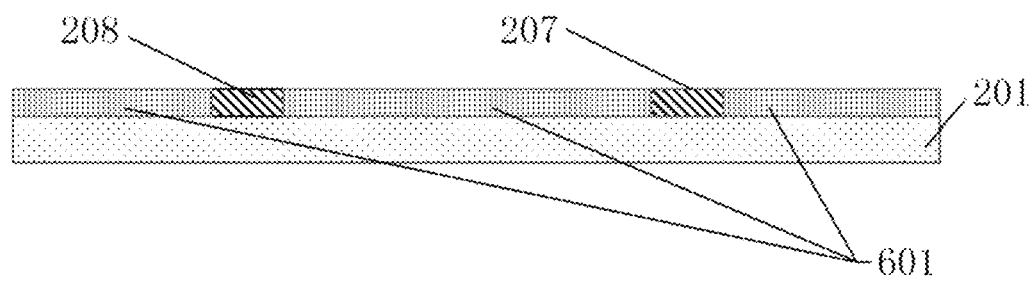
FIG. 5 is an arrangement diagram of an ion selective film and a test electrode on a guide portion in the preferred embodiment of the present invention.
Figure 6:
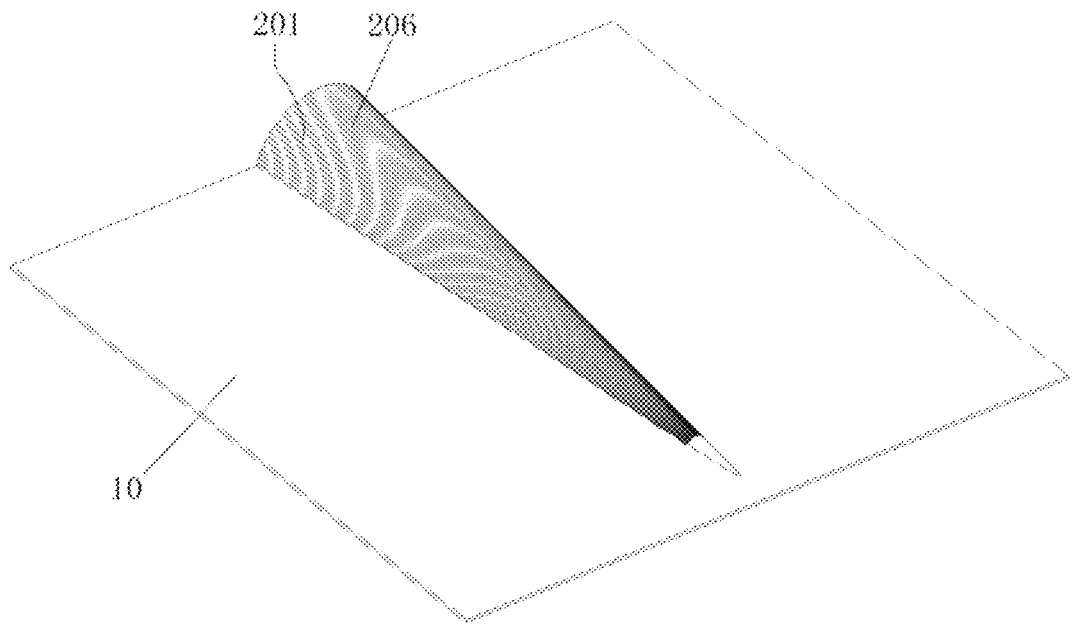
FIG. 6 is a distribution diagram of micro-grooves of a semi-conical structure in the preferred embodiment of the present invention.

In the drawings: 1. detection sensor; 10. base plate; 201. guide portion; 202. outer conical surface; 203. test electrode; 204. back electrode; 206. micro-groove; 207. first test electrode; 208. second test electrode; 30. test element; 301. first voltage test circuit; 302. second voltage test circuit; 401. through hole; 501. medical cotton; 601. ion selective film; 70. protective shell; 72. bearing plate; 80. liquid drop.

DETAILED DESCRIPTION OF PREFERRED EMBODIMENTS

Referring to FIGS. 1 to 6, an embodiment of the present application discloses a wearable passive sweat detection device, including at least one detection sensor 1, wherein the detection sensor 1 includes: a base plate 10; a sensing element provided on the base plate 10, the sensing element including a sweat collection portion and a sweat self-driven detection portion, the sweat collection portion being configured to collect sweat discharged by sweat glands of skin, the sweat self-driven detection portion including a guide portion 201 of a semi-conical structure, a test electrode 203 provided on an outer conical surface 202 of the guide portion 201, and a back electrode 204, and a narrow end of the guide portion 201 facing the sweat collection portion; and a test element 30 connected with the test electrode 203 and the back electrode 204. The guide portion 201 and the back electrode 204 are provided on opposite surfaces of the base plate 10 respectively. In the present embodiment, the guide portion 201 is provided on an upper surface of the base plate 10, and the back electrode 204 is provided on a lower surface of the base plate 10.

Specifically, the sweat collection portion includes a through hole 401 formed on the base plate 10, and the through hole 401 is in direct butt joint with the sweat gland of the skin, such that the sweat discharged from the sweat gland conveniently passes through the through hole 401 and moves from the narrow end to a wide end of the guide portion 201.

Preferably, both the base plate 10 and the guide portion 201 are made of PDMS; since the base plate 10 is made of the PDMS, a wearable demand can be conveniently met by the detection device, and since the guide portion 201 is made of the PDMS, a liquid-solid friction effect can be conveniently generated, and meanwhile, wearability is improved.

Further, the upper surface of the base plate 10 is a flat surface to be fitted with the guide portion 201, and the outer conical surface 202 of the guide portion 201 is a hydrophilic conical surface. The outer conical surface 202 of the guide portion 201 may be uniformly coated with nano-silica, such that the outer conical surface 202 is hydrophilic.

In the present embodiment, the outer conical surface 202 of the guide portion 201 is provided with a plurality of micro-grooves 206 to improve a force of sweat on the outer conical surface 202 and improve detection accuracy.

Specifically, the test electrode 203 includes a first test electrode 207 and a second test electrode 208, the test element 30 includes two voltage test circuits, the two voltage test circuits are a first voltage test circuit 301 and a second voltage test circuit 302, an anode and a cathode of the first voltage test circuit 301 are connected with the first test electrode 207 and the back electrode 204 respectively, and an anode and a cathode of the second voltage test circuit 302 are connected with the second test electrode 208 and the back electrode 204 respectively. The sweat is subjected to voltage detection twice by the first voltage test circuit 301 and the second voltage test circuit 302, such that a moving speed of the sweat can be obtained conveniently, accuracy of a subsequent calibration result can be improved, and a relational expression between a concentration and a voltage can be more accurate; that is, a detection result of the concentration can be more accurate. It may be appreciated that the test element 30 is not limited to the voltage test circuit, and two current test circuits may be employed for the test element 30.

Preferably, the first test electrode 207 and the second test electrode 208 are both electrode wires, and the back electrode 204 is a gold plated layer. The electrode wire is provided on the outer conical surface 202 of the guide portion 201 by electroplating.

To facilitate electrical connection between the first test electrode 207 and the first voltage test circuit 301 and meanwhile facilitate electrical connection between the second test electrode 208 and the second voltage test circuit 302, preferably, both the first test electrode 207 and the second test electrode 208 extend onto the base plate 10.

In the present embodiment, a sweat discharge portion is provided at the wide end of the guide portion 201. Further preferably, the sweat discharge portion is medical cotton 501 which can absorb the sweat flowing therethrough, and meanwhile, the medical cotton avoids a skin allergy and can be replaced regularly.

In order to detect a certain component in the sweat, preferably, an ion selective film 601 is provided on the outer conical surface 202 of the guide portion 201.

In order to avoid contamination of the detection device, a protective shell 70 is preferably provided on the base plate 10.

Figure 7:
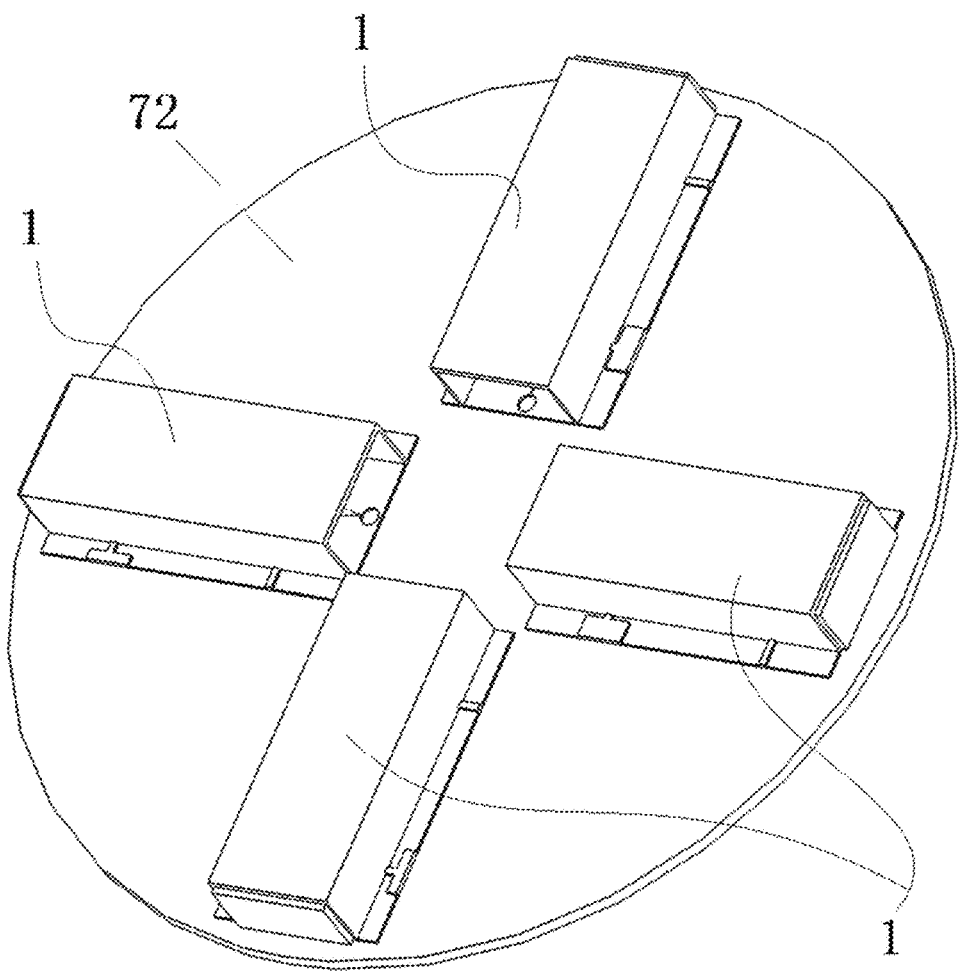
FIG. 7 is a schematic diagram of a multi-parameter parallel detection sensor in the preferred embodiment of the present invention.

In order to detect various ion concentrations at the same time to realize multi-parameter parallel detection, reference is made to FIG. 7, a bearing plate 72 may be provided, a plurality of detection sensors 1 may be arranged on the bearing plate 72, and different ion selective films 601 are used on the detection sensors 1 to detect different ion concentrations. Preferably, the bearing plate 72 is circular, and the plurality of detection sensors 1 are uniformly distributed on the bearing plate 72 circumferentially. The bearing plate 72 is made of PDMS, and the wearability is improved.

Figure 8:
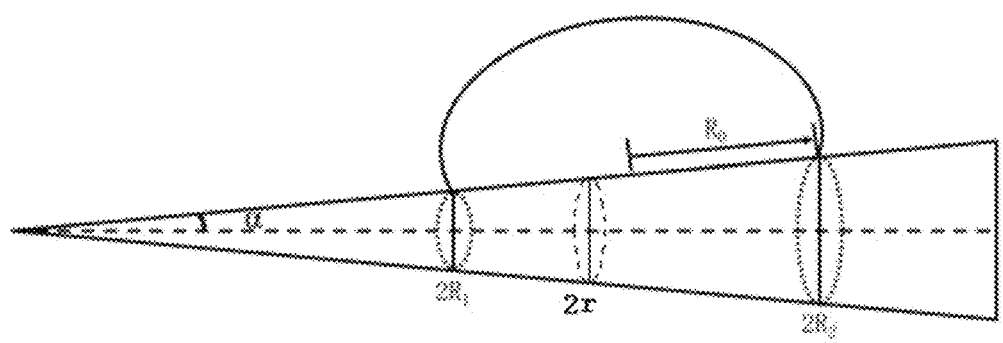
FIG. 8 is a force analysis diagram of a liquid drop on an outer conical surface of a sweat self-driven test portion in the preferred embodiment of the present invention.

The sweat drops on the outer conical surface 202 of the guide portion 201, as shown in FIG. 8 which shows a complete conical structure, and the complete conical structure is divided into two semi-conical structures by a dotted line in FIG. 8, one semi-conical structure is the guide portion 201, and the narrow end of the guide portion 201 refers to a tip of the guide portion 201. Due to asymmetry of a radius of curvature of the liquid drop, a Laplace pressure is generated:

$$\Delta P = \int_{R_1}^{R_2} \frac{2\gamma}{(r+R_0)} \sin\alpha \, dz \tag{1}$$

In the above formula (1), r is a local radius of the semi-conical structure, $R_1$ and $R_2$ are local radii of the semi-conical structure corresponding to two sides of the liquid drop on the semi-conical structure, $R_1 < R_2$, $\gamma$ is surface tension of the sweat drop, R0 is a radius of the liquid drop, a is a semiapex angle of the semi-conical structure, and dz is an increment of the semi-conical structure. A Laplace pressure in a region near the narrow end of the semi-conical structure is greater than that in a region near the wide end of the semi-conical structure; that is, the Laplace pressure at the small radius $R_1$ is greater than that at the large radius $R_2$. An internal Laplace pressure difference ($\Delta P$) resulting from the asymmetry of the curvature of the liquid drop is a motive force to drive the liquid drop to move from the narrow end to the wide end along the guide portion 201 of the semi-conical structure.

In addition to a gradient of the Laplace pressure, a gradient without surface energy is another driving force. Specifically, the micro-groove 206 on the guide portion 201 has a width gradient. The micro-grooves 206 are sparser near the wide end of the guide portion 201 than near the tip of the guide portion 201, and the micro-grooves 206 are denser near the tip of the guide portion 201 than near the wide end of the guide portion 201; that is, the tip of the guide portion 201 is rougher than the wide end of the guide portion 201. According to the Wenzel equation, in formula (2), r is a roughness coefficient defined as a ratio of an actual surface area to a geometric projected area of a rough surface (for a smooth surface, r=1, and for the rough surface, r>1), $\theta_0$ and $\theta_w$ are an intrinsic contact angle and an apparent contact angle respectively, and a gradient of roughness yields a wettability gradient, i.e. the gradient without the surface energy:

$$\cos \theta_w = r \cos \theta_0 \quad (2)$$

The gradient without the surface energy generates the driving force F:

$$F = \int_{l_{base}}^{l_{tip}} \gamma (\cos \theta_a - \cos \theta_r) dl \quad (3)$$

In the formula (3), $\gamma$ is the surface tension of the sweat drop, $\theta_a$ and $\theta_r$ are advancing and retreating contact angles of the liquid drop on the guide portion 201 respectively, and dl is an integral variable between the region $l_{tip}$ near the tip and the region $l_{base}$ near the wide end of the semi-conical structure.

Figure 9:
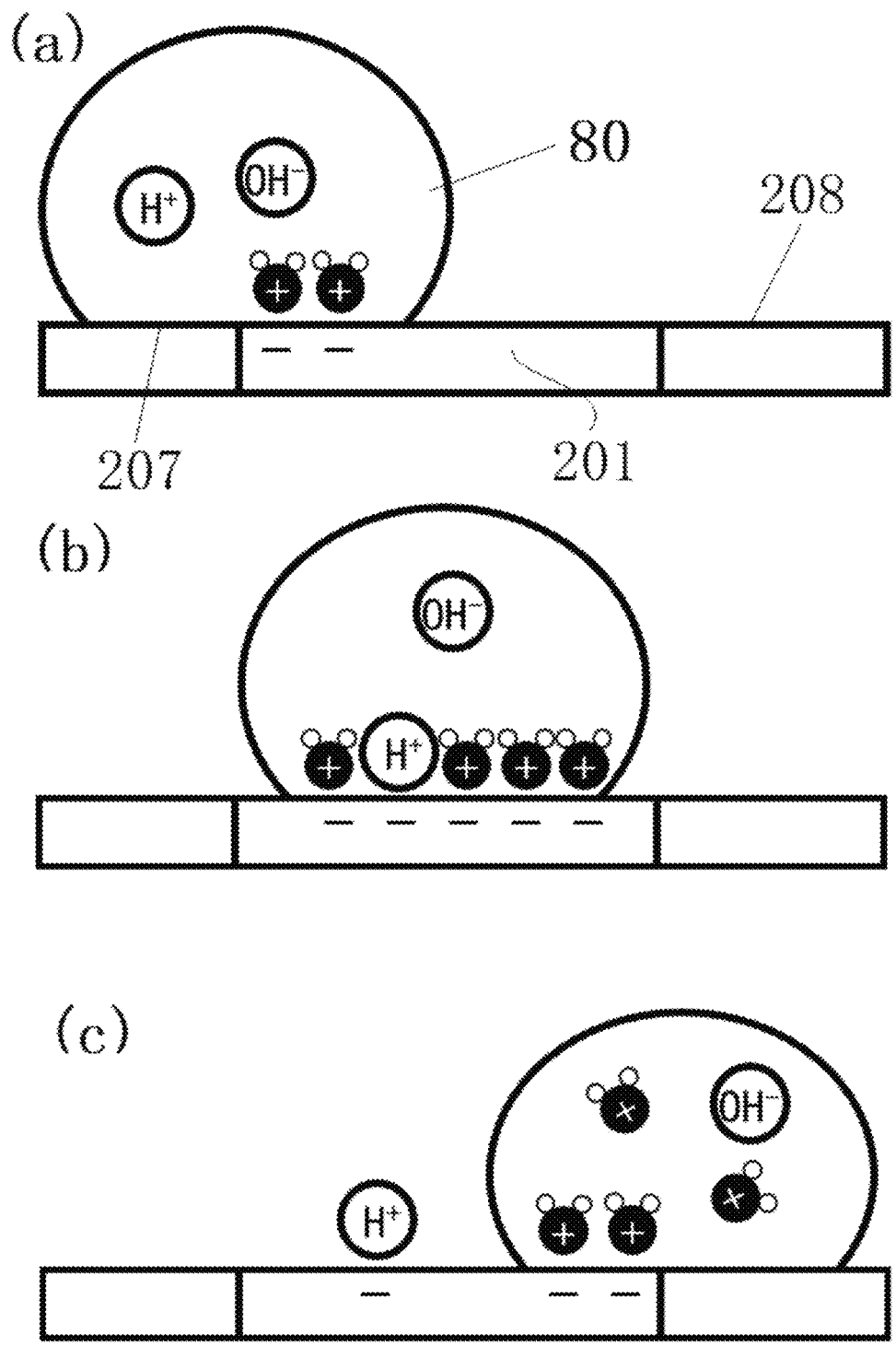
FIG. 9 is a schematic diagram of generation of charges by liquid-solid friction of a distilled water drop in the preferred embodiment of the present invention.
Figure 10:
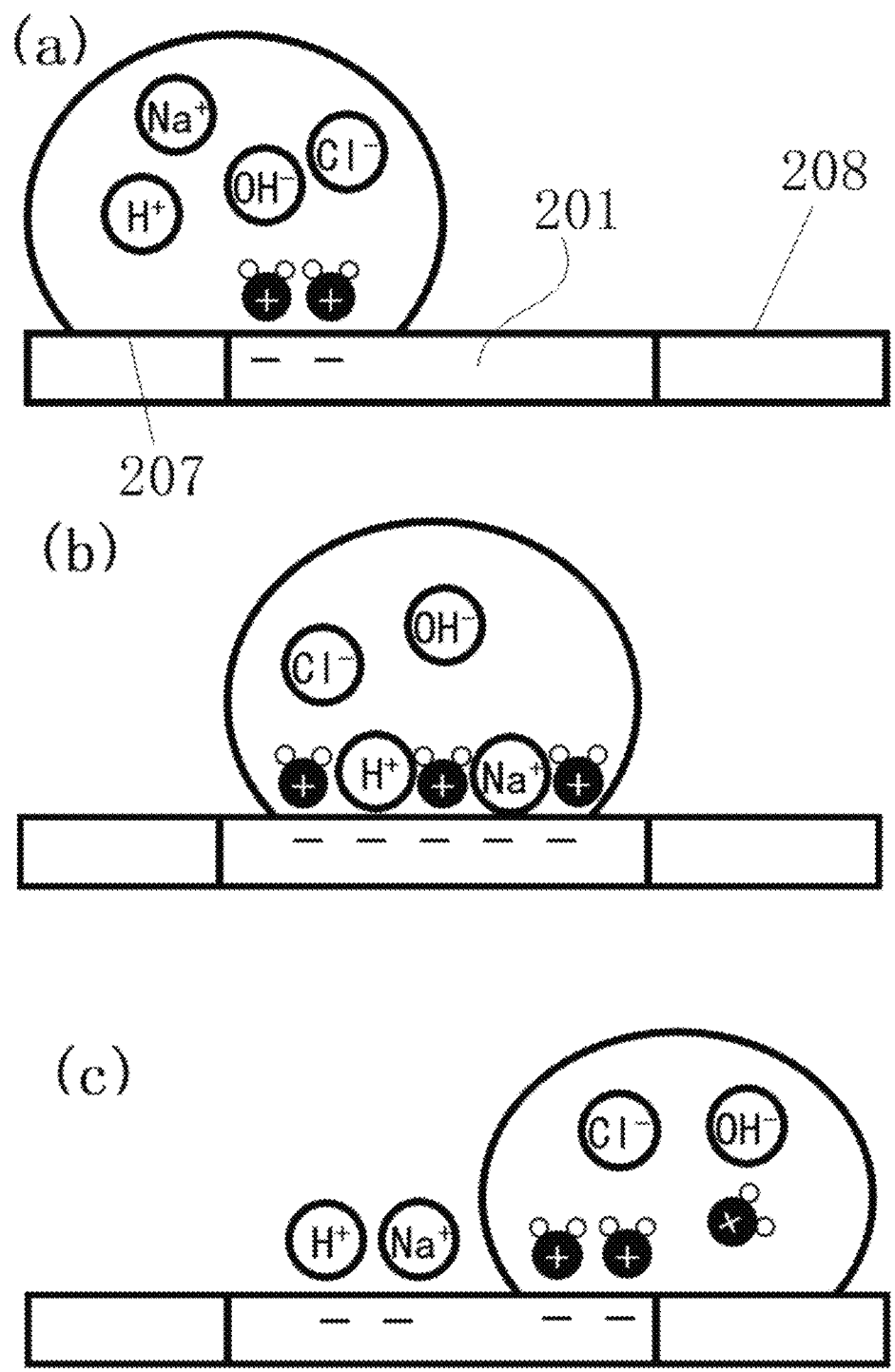
FIG. 10 is a schematic diagram of generation of charges by liquid-solid friction of an ionic solution drop in the preferred embodiment of the present invention.

A process of generating an electric signal by liquid-solid friction and a principle of measuring the concentration thereof are described below, as shown in FIGS. 9 and 10. FIG. 9 is a diagram of a movement process when the liquid drop 80 is distilled water, that is, when other ions do not exist. One part of the liquid drop 80 is located on the first test electrode 207, the other part thereof is located on the PDMS of the guide portion 201, and after the PDMS contacts water molecules, that is, after liquid-solid friction is generated, electrons jump from oxygen atoms of the water molecules to LUMO (an orbit with a lowest energy level and without electrons) of the PDMS, as shown in FIG. 9(a); after the electrons are separated from the water molecules, the electrons remain on the PDMS, the water molecules in contact with the PDMS are positively charged, and since the liquid drop 80 continuously moves on the PDMS to generate liquid-solid friction, the water molecules with positive charges are increased, as shown in FIG. 9(b); after the liquid drop 80 moves continuously, a part of the liquid drop 80 is located on the PDMS of the guide portion 201, the other part thereof moves to the second test electrode 208, and due to polarization, some water molecules are attracted to a surface of the PDMS, the other water molecules are dispersed in water, as shown in FIG. 9(c), and an electric quantity of the dispersed water molecules is an electrical signal to be tested. FIG. 10 shows a diagram of a movement process of a liquid drop containing ions. When an ionic solution comes into contact with the PDMS of the guide portion 201, electron transfer and adsorption occur at a liquid-solid interface, as shown in FIG. 10(a); after the liquid drop completely moves onto the PDMS, as shown in FIG. 10(b), sodium ions in the ionic solution replace the water molecules losing the electrons; that is, positions of the water molecules are occupied by the sodium ions; as shown in FIG. 10(c), polarized water molecules are reduced, the water molecules dispersed in the liquid drop are reduced, and thus, a quantity of tested charges is reduced. That is, the greater the ion concentration, the fewer the polarized water molecules, and the smaller the quantity of the tested charges. Therefore, the charge quantity and the ion concentration have a negative correlation.

As can be seen from the comparison between FIGS. 9 and 10, four positively charged water molecules are in contact with the PDMS in FIG. 9(b) due to absence of other ions, and the positions of the water molecules are occupied in FIG. 10(b) due to presence of Na+, and therefore, only three positively charged water molecules exist, the water molecules dispersed in the liquid drop are reduced, and thus, the charge quantity is reduced. In addition, the arrangement of the ion selective film 601 can ensure that only one type of ions is in contact with the PDMS through the ion selective film 601, and the other ions are blocked; that is, only one type of ions is guaranteed to be attracted to the surface of the PDMS, such that the ions causing the final electrical signal can be determined.

When the sweat detection device is used, a sensing device is stuck to a surface of the skin by medical adhesive tape, the through hole 401 is in butt joint with the sweat gland of the skin, and then, a human body perspires normally in an exercise process or in a high-temperature environment, the sweat enters the sweat self-driven detection portion from the through hole 401, and due to an asymmetric structure, the sweat drop is subjected to a Laplace force, directional movement is realized along the outer conical surface 202 of the guide portion 201, and in the movement process of the sweat drop, due to the liquid-solid friction effect, opposite charges can be carried on surfaces of liquid and solid, and since ions have a shielding effect, that is, occupy the positions of the water molecules in the liquid drop, the greater the ion concentration is, the more obvious the shielding effect is, and therefore, the charge quantity and the ion concentration have the negative correlation; a voltage value can be measured by the first voltage test circuit 301 and the second voltage test circuit 302 to reflect the ion concentration. After the sweat moves from the narrow end to the wide end of the sweat self-driven detection portion, detection is completed, the discharged sweat is absorbed by the medical cotton 501, and the detection process is finished.

It will be evident to those skilled in the art that the invention is not limited to the details of the foregoing illustrative embodiments, and that the present invention may be embodied in other specific forms without departing from the spirit or essential attributes thereof

What is claimed is:

1. A wearable passive sweat detection device, comprising at least one detection sensor, wherein the detection sensor comprises:
    a base plate;
    a sensing element provided on the base plate, the sensing element comprising a sweat collection portion and a sweat self-driven detection portion, the sweat collection portion being configured to collect sweat discharged from sweat glands of skin, the sweat self-driven detection portion comprising a guide portion of a semi-conical structure, a test electrode provided on an outer conical surface of the guide portion and a back electrode, and a narrow end of the guide portion facing the sweat collection portion;
    a test element connected with the test electrode and the back electrode.

2. The wearable passive sweat detection device according to claim 1, wherein the sweat collection portion comprises a through hole formed on the base plate.

3. The wearable passive sweat detection device according to claim 1, wherein both the base plate and the guide portion are made of PDMS.

4. The wearable passive sweat detection device according to claim 1, wherein an upper surface of the base plate is a flat surface and the outer conical surface of the guide portion is a hydrophilic conical surface.

5. The wearable passive sweat detection device according to claim 1, wherein the outer conical surface of the guide portion is provided with a plurality of micro-grooves.

6. The wearable passive sweat detection device according to claim 1, wherein the test electrode comprises a first test electrode and a second test electrode, the test element comprises two voltage test circuits or two current test circuits, an anode and a cathode of one voltage test circuit or current test circuit are connected with the first test electrode and the back electrode respectively, and an anode and a cathode of the other voltage test circuit or current test circuit are connected with the second test electrode and the back electrode respectively.

7. The wearable passive sweat detection device according to claim 6, wherein the first test electrode and the second test electrode are electrode wires and the back electrode is a gold plated layer.

8. The wearable passive sweat detection device according to claim 6, wherein the first test electrode and the second test electrode extend onto the base plate.

9. The wearable passive sweat detection device according to claim 1, wherein a sweat discharge portion is provided at a wide end of the guide portion.

10. The wearable passive sweat detection device according to claim 1, wherein an ion selective film is provided on the outer conical surface of the guide portion.

* * * * *